(12) United States Patent
Tang et al.

(10) Patent No.: US 8,344,007 B2
(45) Date of Patent: Jan. 1, 2013

(54) WATER-SOLUBLE POLYMER-BASED CANTHARIMIDES AS POTENTIALLY SELECTIVE ANTI-TUMOR AGENTS

(75) Inventors: Johnny Cheuk-on Tang, Hong Kong (CN); Albert Sun-chi Chan, Hong Kong (CN); Kim-hung Lam, Hong Kong (CN); Chung-hin Chui, Hong Kong (CN); Stanton Hon Lung Kok, Hong Kong (CN); Marcus Chun Wah Yuen, Hong Kong (CN); Sau Hing Chan, Hong Kong (CN); Chor Hing Cheng, Hong Kong (CN); Filly Cheung, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 186 days.

(21) Appl. No.: 12/428,488

(22) Filed: Apr. 23, 2009

(65) Prior Publication Data

US 2010/0273840 A1   Oct. 28, 2010

(51) Int. Cl.
*A01N 43/78* (2006.01)
*A61K 31/41* (2006.01)
(52) U.S. Cl. ........................ 514/367; 548/159
(58) Field of Classification Search ............ 548/159; 514/367
See application file for complete search history.

(56) References Cited

OTHER PUBLICATIONS

See Schafer et al. Drug Discovery Today 2008, 13 (21/22), 913-916.*
Horig et al Journal of Translational Medicine 2004, 2(44).*
Kok et al "Synthesis and structure evaluation of a novel cantharimide and its cytotoxicity on SK-Hep-1 heptoma cell", Bioorganic & Medicinal chemistry, letters 17, 2007, pp. 115-1159.*
Fabian et al "Azabenzenes (Azines)—The nitrogen derivatives of benzene with one to six N atoms: stability, homodesmotic stabilization energy, electron distribution and magnetic ring current; a computational study", Can. J. Chem. vol. 82, pp. 50-69, 2004.*
Wolff Burger's Medicinal Chemistry and Drug Discovery, Fifth Edition, vol. I: Principles and Practice, Wiley-Interscience 1995, pp. 974-977.*
KoK et al., "Apoptotic activity of a novel synthetic canthraridin analogue on hepatoma cell lines", International Journal of Molecular Medicine, 17: 945-949, 2006.*

* cited by examiner

*Primary Examiner* — Brandon Fetterolf
*Assistant Examiner* — Jean Cornet
(74) *Attorney, Agent, or Firm* — Duane Morris LLP; Siegfried J.W. Ruppert

(57) ABSTRACT

A cantharimide compound may include the backbone of formula (1). $R^1$, $R^2$, $R^3$, and $R^4$ may be independently selected from the group consisting of H, $C(O)OR^5$, $C(O)R^6$, $C(O)NR^7R^8$, $NR^9C(O)R^{10}$, $N-R^{11}R^{12}$, $O-R^{13}$, $S-R^{14}$, $P(O)(OR^{15})(OR^{16})$, $As(O)(OR^{17})(OR^{18})$, $SO_2R^{19}$, $SO_3R^{20}$, and $B(OR^{21})$. $X^1$ to $X^4$ may be independently selected from the group consisting of nitrogen and carbon, such that $X^1$ to $X^4$ are not all hydrogen. $Y^1$, $Y^2$ and $R^5$ to $R^{21}$ may be independently selected from the group consisting of hydrogen, $C_{1-12}$-alkyl, -aryl, heteroaryl, and a bioactive polymer.

formula (1)

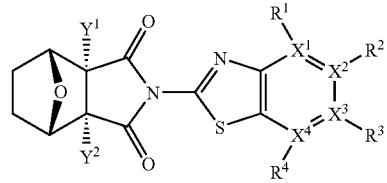

19 Claims, 3 Drawing Sheets

WATER-SOLUBLE POLYMER-BASED CANTHARIMIDES AS POTENTIALLY SELECTIVE ANTI-TUMOR AGENTS

BACKGROUND

Cantharidin (exo,exo-2,3-dimethyl-7-oxobicyclo[2.2.1] heptane-2,3-dicarboxylic acid anhydride) is an active ingredient isolated from the Chinese blister beetles *Mylabris phalerata* or *M. cichorii*. Cantharidin has been reported to be active against various human cancers. Cantharidin's severe renal toxicity, however, limits its development as a chemotherapeutic agent. Moreover, although numerous physiological and biochemical studies have been carried out in an attempt to find the cause of growth inhibition and cell death provided by cantharidin, the critical molecular mechanism of action and pathways remain unclear.

Various derivatives of cantharidin have been investigated as potential anti-tumor agents. Synthetic norcantharidin derivatives are demethylated analogs of cantharidin. These derivatives have clinical potential as a result of causing similar growth inhibition activity as cantharidin, but have a strong suppression of renal and gastrointestinal toxicity. Cantharidic acid represents the first commercialized cantharidic anti-tumor agent to date. However, these compounds are limited by their toxicity towards the normal cells that prevent them from being effective anti-cancer drugs or chemotherapy in cancer treatment.

Consequently, it is desirable to synthesize new cantharimide compounds as cantharidin-mimics with anti-tumor effect. It is also desirable that the compounds have enhanced cytotoxicity to cancer cells, while simultaneously having reduced toxicity for normal cells. Such compounds could be useful in anti-cancer drugs or chemotherapy in cancer treatment.

BRIEF SUMMARY

According to one aspect, a cantharimide compound may include the backbone of formula (1):

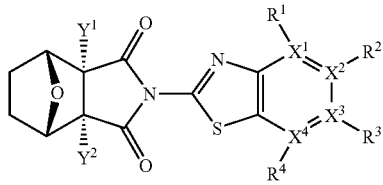

$R^1$, $R^2$, $R^3$, and $R^4$ may be independently selected from the group consisting of H, $C(O)OR^5$, $C(O)R^6$, $C(O)NR^7R^8$, $NR^9C(O)R^{10}$, $N-R^{11}R^{12}$, $O-R^{13}$, $S-R^{14}$, $P(O)(OR^{15})(OR^{16})$, $As(O)(OR^{17})(OR^{18})$, $SO_2R^{19}$, $SO_3R^{20}$, and $B(OR^{21})$. $X^1$-$X^4$ may be independently selected from the group consisting of nitrogen and carbon. $R^1$ to $R^4$ may not be all hydrogen. $Y^1$, $Y^2$ and $R^5$ to $R^{21}$ may be independently selected from the group consisting of hydrogen, $C_{1-12}$-alkyl, -aryl, heteroaryl, and a bioactive polymer.

According to another aspect, a method for treating an adverse health condition in a subject may include administering an effective amount of a cantharimide compound of formula (1) to the subject.

Accordingly to a further aspect, a method of making a cantharimide compound may include preparing a 2-aminobenzothiazole compound and condensing the 2-amino-benzothiazole compound with a cantharidin in the presence of a toluene-triethylamine mixture.

DETAILED DESCRIPTION

Figure 1:
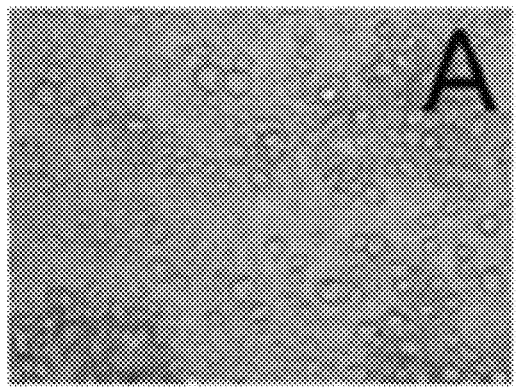
FIG. 1A depicts an image of untreated non-malignant haematological disorder bone marrow.
FIG. 1B depicts an image of non-malignant haematological disorder bone marrow treated with 5 g/ml of dicantharidic acid.
FIG. 1C depicts an image of non-malignant haematological disorder bone marrow treated with 5 g/ml of CAN039.
FIG. 1D depicts an image of untreated KG1a acute myelogenous leukemia cell line.
FIG. 1E depicts an image of KG1a acute myelogenous leukemia cell line treated with 5 g/ml of dicantharidic acid.
FIG. 1F depicts an image of KG1a acute myelogenous leukemia cell line treated with 5 g/ml of CAN039.
Figure 1:
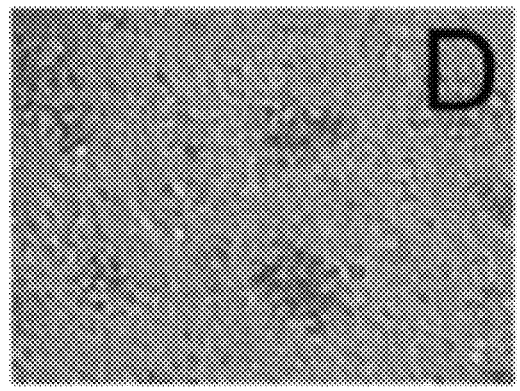
Figure 1:
Figure 1:
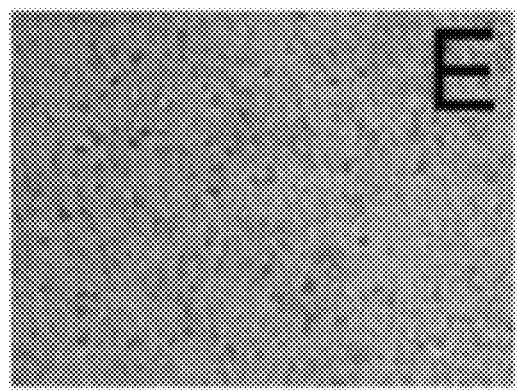
Figure 1:
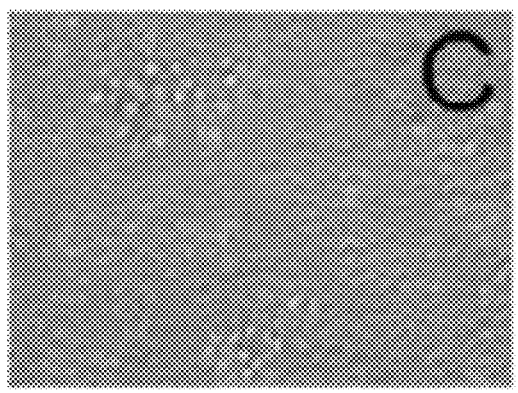
Figure 1:
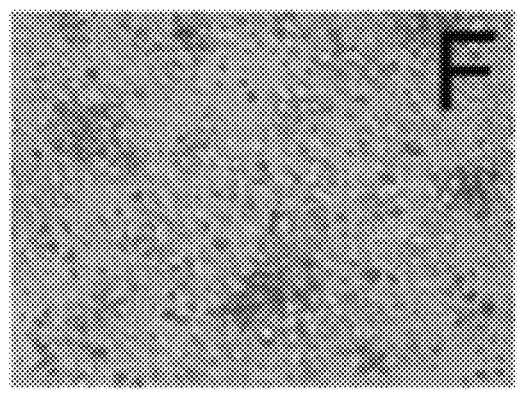

Reference will now be made in detail to a particular embodiment of the invention, examples of which are also provided in the following description. Exemplary embodiments of the invention are described in detail, although it will be apparent to those skilled in the relevant art that some features that are not particularly important to an understanding of the invention may not be shown for the sake of clarity.

Furthermore, it should be understood that the invention is not limited to the precise embodiments described below, and that various changes and modifications thereof may be effected by one skilled in the art without departing from the spirit or scope of the invention. For example, elements and/or features of different illustrative embodiments may be combined with each other and/or substituted for each other within the scope of this disclosure and appended claims. In addition, improvements and modifications which may become apparent to persons of ordinary skill in the art after reading this disclosure, the drawings, and the appended claims are deemed within the spirit and scope of the present invention.

TERMINOLOGY AND ABBREVIATIONS

As used herein, the term "disorder" refers to a medical disorder of an organism. Examples of disorders include a proliferative disorder, a cancer, an inflammatory disorder, or one or more symptoms thereof.

As used herein, the term "effective amount" refers to the amount of a compound that is sufficient to reduce or ameliorate the severity or duration of a disorder, to prevent the advancement of a disorder, to cause regression of a disorder, to prevent the recurrence, development, or onset of one or more symptoms associated with a disorder, or to enhance or improve the prophylactic or therapeutic effect(s) of another therapy.

As used herein, the term "in combination" refers to the use of more than one therapy. The use of the term "in combination" does not restrict the order in which therapies are administered to a subject with a disorder. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a disorder.

As used herein, the terms "manage," "managing," and "management" refer to the beneficial effects that a subject derives from a therapy while not resulting in a cure of the disease. In certain embodiments, a subject is administered one or more therapies "manage" a disease so as to prevent the progression or worsening of the disease.

As used herein, the phrase "pharmaceutically acceptable salt" refers to pharmaceutically acceptable organic or inorganic salts of a compound. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylenebis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure, in which case the pharmaceutically acceptable salt can have multiple counterions. Hence, a pharmaceutically acceptable salt can have one or more charged atoms and/or one or more counterions.

As used herein, the term "pharmaceutically acceptable solvate" refers to an association of one or more solvent molecules and a cantharimide compound. Examples of solvents that form pharmaceutically acceptable solvates include, but are not limited to, water, isopropanol, ethanol, methanol, DMSO, ethyl acetate, acetic acid, and ethanolamine.

As used herein, the terms "prophylactic agent" and "prophylactic agents" refer to any agent(s) which can be used in the prevention of a disorder or one or more symptoms thereof. In certain embodiments, the term "prophylactic agent" refers to a cantharimide compound. In certain other embodiments, the term "prophylactic agent" refers to a compound other than a cantharimide compound. Prophylactic agents may be characterized as different agents based upon one or more effects that the agents have in vitro and/or in vivo.

As used herein, the terms "prevent," "preventing" and "prevention" refer to the prevention of the recurrence, onset, or development of a disorder or a symptom thereof in a subject resulting from the administration of a therapy, or the administration of a combination of therapies.

An adverse effect from a therapy might be harmful, uncomfortable and/or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra pyramidal symptoms, akathisia, cardiovascular disturbances and sexual dysfunction.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a monkey such as a cynomolgous monkey, a chimpanzee and a human), and more preferably a human. In one embodiment, the subject is refractory or non-responsive to current treatments for a disorder. In another embodiment, the subject is an animal that is treated by a veterinarian, such as a farm animal (e.g., a horse, a cow, a pig, etc.) or a pet (e.g., a dog or a cat). In another embodiment, the subject is an animal, preferably a mammal, and more preferably a human, that is predisposed and/or at risk because of a genetic factor(s), an environmental factor(s), or a combination thereof, to develop a disorder.

As used herein, the term "synergistic" refers to a combination of cantharimide compounds of and/or a combination of a compound or compounds and another therapy, including one which has been or is currently being used to prevent, manage or treat a disorder, which combination is more effective than the additive effects of the individual compounds or therapies. A synergistic effect of a combination of therapies can permit the use of lower dosages of one or more of the therapies and/or less frequent administration of said therapies to a subject with a disorder. The ability to utilize lower dosages of a therapy and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Moreover, a synergistic effect of a combination of therapies can avoid or reduce adverse or unwanted side effects associated with the use of either therapy alone.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a cantharimide compound. In certain other embodiments, the term "therapeutic agent" refers to a compound other than a cantharimide compound. Therapeutic agents may be characterized as different agents based upon one or more effects the agents have in vivo and/or in vitro, for example, an anti-inflammatory agent may also be characterized as an immunomodulatory agent.

As used herein, the term "therapeutically effective amount" refers to that amount of a therapy sufficient to result in the amelioration of one or more symptoms of a disorder, prevent advancement of a disorder, cause regression of a disorder, or to enhance or improve the therapeutic effect(s) of another therapy.

In a specific embodiment, with respect to the treatment of cancer, an effective amount refers to the amount of a therapy that inhibits or reduces the proliferation of cancerous cells; inhibits or reduces the spread of tumor cells (metastasis); inhibits or reduces the onset, development or progression of cancer or a symptom thereof; or reduces the size of a tumor. Preferably, a therapeutically effective amount of a therapy reduces the proliferation of cancerous cells or the size of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control, or to a placebo such as phosphate buffered saline ("PBS").

As used herein, the terms "therapies" and "therapy" can refer to any protocol(s), method(s), and/or agent(s) that can be used in the prevention, treatment, management, or amelioration of a disorder or one or more symptoms thereof. In certain embodiments, the terms "therapy" and "therapies" refer to chemotherapy, radiation therapy, hormonal therapy, biological therapy, and/or other therapies useful in the prevention, management, treatment or amelioration of a disorder or one or more symptoms thereof known to one of skill in the art such as skilled medical personnel.

As used herein, the terms "treat", "treatment" and "treating" refer to the reduction or amelioration of the progression, severity and/or duration of a disorder, or the amelioration of one or more symptoms thereof resulting from the administration of one or more therapies. In specific embodiments, such terms refer to the inhibition or reduction in the proliferation of cancerous cells, the inhibition or reduction in the spread of tumor cells (metastasis), the inhibition or reduction in the onset, development or progression of cancer or a symptom thereof, the reduction in the size of a tumor, or the improvement in a patient's Karnofsky score.

The Composition

The cantharimide compounds may include the backbone of formula (1):

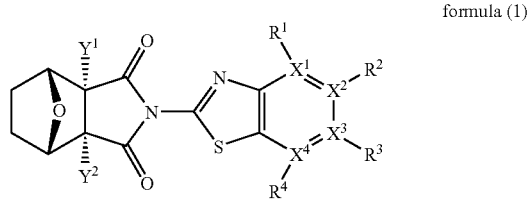

$R^1$, $R^2$, $R^3$, and $R^4$ may be independently selected from the group consisting of H, C(O)OR$^5$, C(O)R$^6$, C(O)NR$^7$R$^8$, NR$^9$C(O)R$^{10}$, N—R$^{11}$R$^{12}$, O—R$^{13}$, S—R$^{14}$, P(O)(OR$^{15}$)(OR$^{16}$), As(O)(OR$^{17}$)(OR$^{18}$), SO$_2$R$^{19}$, SO$_3$R$^{20}$, and B(OR$^{21}$). $X^1$ to $X^4$ may be independently nitrogen, or carbon, such that $X^1$ to $X^4$ are not all hydrogen. $Y^1$, $Y^2$ and $R^5$ to $R^{21}$ may be independently selected from the group consisting of hydrogen, $C_{1-12}$-alkyl, aryl, heteroaryl, and a bioactive polymer.

The bioactive polymer may include a propionate or butanoate acid moiety attached to a terminal end (ω-position) of a polymer moiety selected from the group consisting of poly(alkylene oxides), poly(oxyethylated polyols), and poly(olefinic alcohols). The polymer moiety may have about 2 to more than 300 recurring monomer units.

In one embodiment, there is provided a composition comprising a mixture of cantharimides or a pharmaceutically acceptable salt, solvate or hydrate thereof. In one embodiment, the cantharimides in a composition constitutes at least about 10%, at least about 20%, at least about 25%, at least about 35%, at least about 50%, at least about 75%, at least about 80%, or at least about 90% of the total content in the composition.

Agents Useful in Combination with the Compounds

There is provided methods for preventing, managing, treating, or ameliorating a proliferative disorder or a cancer comprising administering to a subject in need thereof a cantharimide composition and one or more therapies other than the cantharimide compounds.

Any agent that contributes to the prevention, management, treatment, or amelioration of a proliferative disorder or a cancer, or one or more symptoms thereof may be used in combination with a cantharimide composition described herein. Therapeutic or prophylactic agents may be used for preventing, treating, managing, or ameliorating proliferative disorders or cancers or one of more symptoms thereof.

Therapeutic or prophylactic anti-cancer agents may include peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies. In certain embodiments, the anti-cancer agent may be a chemotherapeutic agent. In specific embodiments, the anti-cancer agent is an anti-angiogenic agent. In other embodiments, the anti-cancer agent is not an anti-angiogenic agent.

Examples of anti-cancer agents may include acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin-2 (including recombinant interleukin 2, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other examples of anti-cancer drugs may include 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; Avastin®; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

In a specific embodiment, radiation therapy may include the use of x-rays, gamma rays and other sources of radiation to destroy the cancer cells is used in combination with antibodies. In preferred embodiments, the radiation treatment is administered as external beam radiation or teletherapy, wherein the radiation is directed from a remote source. In other preferred embodiments, the radiation treatment is administered as internal therapy or brachytherapy wherein a radioactive source is placed inside the body, close to cancer cells or a tumor mass.

Uses of Cantharimides

Adverse health conditions, diseases and disorders which can be prevented, treated, managed, or ameliorated by administering an effective amount of cantharimides or cantharimide compositions include proliferative disorders and cancers, and symptoms thereof.

The cantharimide compounds and compositions including the cantharimide compounds may be used to prevent, treat, manage, or ameliorate a proliferative disorder or one or more symptoms thereof. A method for preventing, treating, managing, or ameliorating one or more symptoms of cellular hyperproliferation, particularly of epithelial cells (e.g., lymphoproliferative disorder), includes administering to a subject in need thereof a cantharimide compound. A method for preventing, managing, treating, or ameliorating a pre-cancerous disorder associated with cellular hyperproliferation, includes administering to a subject in need thereof one or more cantharimide compounds and one or more other therapies useful for the prevention, treatment, management, or amelioration of the disorder. One or more of the cantharimide compounds may also be used in combination with an anti-cancer therapy, such as radiation therapy.

A method for preventing, managing, treating, or ameliorating a non-cancerous disorder associated with cellular hyperproliferation, or one or more symptoms thereof, includes administering to a subject in need thereof a prophylactically or therapeutically effective amount of a cantharimide composition.

A method for preventing, treating, managing, or ameliorating one or more symptoms of a disorder associated with cellular hyperproliferation in a subject refractory to conventional therapies for such disorder includes contacting the subject with, or administering to the subject, a dose of a prophylactically or therapeutically effective amount of one or more cantharimide compounds. A method for preventing, managing, treating, or ameliorating a non-cancerous disorder associated with cellular hyperproliferation in a subject refractory to conventional therapies for such disorder, includes administering to a subject in need thereof one or more cantharimide compounds and one or more other therapies useful for the prevention, treatment, management, or amelioration of said disorder. Non-limiting examples of such therapies include anti-cancer agents. The cantharimide compositions may also be used in combination with an anti-cancer therapy such as radiation therapy or surgery.

A method for preventing, treating, managing, or ameliorating cancer or one or more symptoms thereof, includes administering to a subject in need thereof a composition comprising cantharimides. A method for preventing, treating, managing, or ameliorating cancer includes administrating one or more compounds in combination with one or more other therapies useful for the prevention, treatment, management, or amelioration of cancer or a secondary condition. The cantharimide compositions may also be used in combination with an anti-cancer therapy such as radiation therapy or surgery.

A method of preventing, treating, managing, or ameliorating cancer or one or more symptoms thereof, includes administering to a subject in need thereof a dose of a prophylactically or therapeutically effective amount of one or more cantharimide compounds. A method of preventing, treating, managing, or ameliorating cancer or one or more symptoms thereof, includes administering to a subject in need thereof a dose of a prophylactically or therapeutically effective amount of one or more cantharimide compounds and a dose of a prophylactically or therapeutically effective amount of one or more therapies useful for the prevention, treatment, management, or amelioration of cancer, or a secondary condition (e.g., a viral, bacterial, or fungal infection).

The cantharimide compounds may be used in in vitro or ex vivo for the management, treatment or amelioration of certain cancers, including leukemias, lymphomas, and human hepatocellular carcinoma xenograft.

One or more of the cantharimide compounds may be used as a first, second, third, fourth, fifth or more line of cancer therapy. A method for preventing, treating, managing, or ameliorating cancer or one or more symptoms thereof in a subject refractory to conventional therapies for such a cancer, includes administering to said subject a dose of a prophylactically or therapeutically effective amount of one or more cantharimide compounds. A cancer may be determined to be refractory to a therapy means when at least some significant portion of the cancer cells are not killed, or are not subject to an arrest of their cell division, in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory to a treatment when the number of cancer cells has not been significantly reduced, or has increased, in response to the treatment.

A method for preventing, managing, treating or ameliorating cancer or one or more symptoms thereof in a subject refractory to existing single agent therapies for such a cancer, including administering to the subject a dose of a prophylactically or therapeutically effective amount of one or more cantharimide compounds and a dose of a prophylactically or therapeutically effective amount of one or more therapies useful for the prevention, treatment, management, or amelioration of cancer or a secondary condition. A method for preventing, treating, managing, or ameliorating cancer or a secondary condition includes administering one or more cantharimide compounds in combination with any other therapy(ies) to patients who have proven refractory to other treatments but are no longer on this therapy(ies).

A method for the prevention, treatment, management, or amelioration of cancer where chemotherapy, radiation therapy, hormonal therapy, and/or biological therapy/immunotherapy has proven or may prove too toxic, i.e., results in unacceptable or unbearable side effects, for the subject being treated, includes administering one or more cantharimide compounds. A method for preventing the recurrence of cancer in patients that have been treated and have no disease activity may include administering one or more cantharimide compounds.

Cancers that can be prevented, managed, treated or ameliorated in accordance with these methods include neoplasms, tumors (malignant and benign) and metastases, or any disease or disorder characterized by uncontrolled cell growth. The cancer may be a primary or metastatic cancer. Specific examples of cancers that can be prevented, managed, treated or ameliorated in accordance with the methods may include leukemia, breast cancer, prostate cancer, colon cancer, lung cancer, melanoma, liver cancer, kidney cancer, brain cancer and gastric cancer.

Lymphoproliferatve diseases that can be treated or prevented using a cantharimide composition include acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; and heavy chain disease.

Breast cancers that can be treated or prevented using a cantharimide composition include adenocarcinoma, lobular (small cell) carcinoma, intraductal carcinoma, medullary breast cancer, mucinous breast cancer, tubular breast cancer, papillary breast cancer, Paget's disease, and inflammatory breast cancer.

Stomach cancers that can be treated or prevented using a cantharimide composition include adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; lung cancers such as non-small cell lung cancer, squamous cell carcinoma (epidermoid carcinoma), adenocarcinoma, large-cell carcinoma and small-cell lung cancer; prostate cancers such as but not limited to, adenocarcinoma, leiomyosarcoma, and rhabdomyosarcoma; skin cancers such as but not limited to, basal cell carcinoma, squamous cell carcinoma and melanoma, superficial spreading melanoma, nodular melanoma, lentigo malignant melanoma, acral lentiginous melanoma; and thyroid cancer such as but not limited to papillary or follicular thyroid cancer, medullary thyroid cancer and anaplastic thyroid cancer.

Compositions and Methods for Administration

Compositions for the treatment, prophylaxis, and amelioration of proliferative disorders and cancers may include cantharimide compositions. Depending on the manner of use, the cantharimide compositions may be in the form of a dietary supplement, a food additive, a pharmaceutical composition, or a cosmetic composition. A cantharimide composition may includes a cantharimide, or a pharmaceutically acceptable salt, solvate, polymorph, or hydrate thereof, and may further include one or more prophylactic or therapeutic agents known to be useful for, having been used for, or currently being used for the prevention, treatment, management, or amelioration of a proliferative disorder or cancer.

Generally, a dietary supplement is consumed by a subject independent of any food composition, unlike a food additive that is incorporated into a food composition during the processing, manufacture, preparation, or delivery of the food composition, or just before its consumption. Accordingly, a food composition provides, in addition to nutrition, a therapeutic or prophylactic function to the consumer. In a specific embodiment, a cantharimide composition is a food composition including a prophylactically or therapeutically effective amount of one or more prophylactic or therapeutic agents. The cantharimide composition may include one or more consumable fillers or carriers. The term "consumable" means the filler or carrier that is generally suitable for, or is approved by a regulatory agency of the Federal or a state government for, consumption by animals, and more particularly by humans. In certain embodiments, the meaning of the term "dietary supplement" or "food additive" is the meaning of those terms as defined by a regulatory agency of the Federal or a state government, including the United States Food and Drug Administration.

A cantharimide composition may be a pharmaceutical composition or a single unit dosage form. Pharmaceutical compositions and single unit dosage forms may include a prophylactically or therapeutically effective amount of one or more prophylactic or therapeutic agents, and typically one or more pharmaceutically acceptable carriers or excipients. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including oils of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, oil, ethanol and the like. Whether a particular excipient is suitable for incorporation into a pharmaceutical composition or dosage form depends on a variety of factors well known in the art, including the way in which the dosage form will be administered to a patient, and the specific active ingredients in the dosage form. The composition or single unit dosage form, if desired, can also contain minor amounts of other ingredients, such as wetting or emulsifying agents, or pH buffering agents.

Lactose-free cantharimide compositions may comprise excipients that are well known in the art. In general, lactose-free cantharimide compositions may include an active ingredient, a binder/filler, and a lubricant in pharmaceutically compatible and pharmaceutically acceptable amounts. Preferred lactose-free dosage forms may include an active ingredient, microcrystalline cellulose, pre-gelatinized starch, and magnesium stearate.

A cantharimide composition may include anhydrous pharmaceutical compositions and dosage forms comprising active ingredients, since water can facilitate the degradation of some compounds. For example, the addition of water (such as 5%) is widely accepted in the pharmaceutical arts as a means of simulating long-term storage in order to determine characteristics such as shelf-life or the stability of formulations over time. In effect, water and heat can accelerate the decomposition of some compounds. The effect of water on a formulation can be of great significance, since moisture and/or humidity are commonly encountered during manufacture, handling, packaging, storage, shipment, and use of formulations.

Anhydrous pharmaceutical compositions and dosage forms may be prepared using anhydrous or low moisture containing ingredients, and low moisture or low humidity conditions. Pharmaceutical compositions and dosage forms that include lactose and at least one active ingredient that includes a primary or secondary amine are preferably anhydrous if substantial contact with moisture and/or humidity during manufacturing, packaging, and/or storage is expected.

Preferably, an anhydrous pharmaceutical composition is prepared and stored such that its anhydrous nature is maintained. Accordingly, anhydrous compositions are preferably packaged using materials known to prevent exposure to water, such that they can be included in suitable formulary kits. Examples of suitable packaging include hermetically sealed foils, plastics, unit dose containers (e.g., vials), blister packs, and strip packs.

A cantharimide composition may include pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, and magnesium carbonate. Such compositions and dosage forms preferably contain a prophylactically or therapeutically effective amount of a prophylactic or therapeutic agent preferably in purified form, together with a suitable amount of carrier, so as to provide the form for proper administration to the patient. The formulation preferably suits the mode of administration. In a preferred embodiment, the pharmaceutical compositions or single unit dosage forms are sterile and in suitable form for administration to a subject, preferably an animal subject, more preferably a mammalian subject, and most preferably a human subject.

A pharmaceutical composition may be formulated to be compatible with its intended route of administration. Examples of routes of administration include parenteral, e.g., intravenous, intradermal, subcutaneous, oral (e.g., inhalation), intranasal, transdermal (topical), transmucosal, intratumoral, intra-synovial and rectal administration. In a specific example, the composition is formulated in accordance with routine procedures as a pharmaceutical composition adapted for intravenous, subcutaneous, intramuscular, oral, intranasal or topical administration to human beings. Preferably, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Examples of dosage forms include tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols, such as nasal sprays or inhalers; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms may vary depending on their use. For example, a dosage form used in the acute treatment of inflammation or a related disorder may contain larger amounts of one or more of the active ingredients it comprises than a dosage form used in the chronic treatment of the same disease. Also, the prophylactically and therapeutically effective dosage form may vary among different types of cancer. Similarly, a parenteral dosage form may contain smaller amounts of one or more of the active ingredients than an oral dosage form used to treat the same disease or disorder. These and other ways in which specific dosage forms encompassed by this application will vary from one another will be readily apparent to those skilled in the art.

The ingredients of compositions may be supplied either separately or mixed together in unit dosage form. The ingredients may be supplied as a dry lyophilized powder or a water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Typical dosage forms of a cantharimide compound, or a pharmaceutically acceptable salt, solvate or hydrate thereof, lie within the range of from about 1 mg to about 1000 mg per day. The dosage for may be given as a single once-a-day dose in the morning, preferably as divided doses throughout the day, taken with food.

Oral Dosage Forms

Pharmaceutical compositions that are suitable for oral administration, and orally comsumable compositions including dietary supplements, can be presented as discrete dosage forms, such as tablets (e.g., chewable tablets), caplets, capsules, and liquids (e.g., flavored syrups). Such dosage forms may contain predetermined amounts of active ingredients, and may be prepared by methods of pharmacy well known to those skilled in the art.

Typical oral dosage forms may be prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include water, glycols, oils, alcohols, flavoring agents, preservatives, and coloring agents. Examples of excipients suitable for use in solid oral dosage forms (e.g., powders, tablets, capsules, and caplets) include starches, sugars, micro-crystalline cellulose, diluents, granulating agents, lubricants, binders, and disintegrating agents. Other ingredients that can be incorporated into a dietary supplement or pharmaceutical compositions of the cantharimide may include vitamins, amino acids, an antioxidant, a botanical extract, metal salts, and minerals.

Because of their ease of administration, tablets and capsules typically represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation, if necessary.

For example, a tablet can be prepared by compression or by molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include binders, fillers, disintegrants, and lubricants. Binders suitable for use in pharmaceutical/nutraceutical compositions and dosage forms include corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions, dietary supplements, and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the cantharimide may be present in from about 50 to about 99 weight percent of the pharmaceutical composition, dietary supplement, or dosage form.

Suitable forms of microcrystalline cellulose include the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants may be used in the cantharimide compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant, that is neither too much nor too little to detrimentally alter the release of the active ingredients, should be used to form solid oral dosage forms. The amount of disintegrant used varies based upon the type of formulation, and is readily discernible to those of ordinary skill in the art. Typical pharmaceutical compositions include from about 0.5 to about 15 weight percent of disintegrant, specifically from about 1 to about 5 weight percent of disintegrant.

Disintegrants that can be used in pharmaceutical compositions, dietary supplements and dosage forms include agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions, dietary supplments, and dosage forms include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions, dietary supplmenents, or dosage forms into which they are incorporated.

Delayed Release Dosage Forms

Active ingredients of the cantharimide compositions can be administered by controlled release means or by delivery devices that are well known to those of ordinary skill in the art. Such dosage forms can be used to provide slow or controlled-release of one or more active ingredients. Examples of controlled-release materials include hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients. Cantharimide compositions thus may be in the form of single unit dosage forms suitable for oral administration such as tablets, capsules, gelcaps, and caplets that are adapted for controlled-release.

Controlled-release pharmaceutical products and dietary supplements typically have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side effects.

Most controlled-release formulations are designed to initially release an amount of a drug (active ingredient) that promptly produces the desired therapeutic effect, and gradually and continually releases lower amounts of the drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Compounds that increase the solubility of one or more of the active ingredients disclosed herein can also be incorporated into the parenteral dosage forms.

Suitable vehicles that can be used to provide parenteral dosage forms of the cantharimide are well known to those skilled in the art. Examples include water for injection USP; aqueous vehicles such as sodium chloride injection, ringer's injection, dextrose injection, dextrose and sodium chloride injection, and lactated ringer's injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Dietary Supplements, Food Additives, Food Compositions

Food compositions may include a cantharimide composition or compound. The term "food compositions of the cantharimide" include any substances—raw, prepared or processed—which are intended for animal or human consumption, in particular by eating or drinking, and which contain nutrients in the form of carbohydrates, proteins and/or fats, and which have been modified by the incorporation of a cantharimide composition, or at least one, two, three, or four compounds of the cantharimide. A food composition of the cantharimide can provide an additional benefit other than its nutritional benefit, specifically that the food composition may be used as an anti-cancer agent.

A cantharimide composition may be a food additive. A food additive can be in solid form or liquid form. For example, a food additive may be a reconstitutable powder that, when reconstituted with a liquid, such as drinking water, can provide a beverage. In another embodiment, a cantharimide composition or compound may be incorporated into other foodstuffs, such as cooking oil, frying oil, salad oil, margarine, mayonnaise or peanut butter. Oils containing the cantharimide compounds can be emulsified and used in a variety of water-based foodstuffs, such as drinks. Food compositions including cantharimide compositions and compounds may be a beverage, such as fortified mineral water, fortified distilled water, a fruit juice-based beverage, a shake, a milk-based beverage, a dairy product-based beverage, a yoghurt-based beverage, a carbonated water-based beverage, an alcoholic drink, a coffee-based beverage, a green tea-based beverage, a black tea-based beverage, a grain-based beverage, a soybean-based beverage, or a beverage based on plant extracts.

In addition to beverages, the cantharimide compositions may be used as a food additive to be combined with other foodstuffs, for example, syrups, starches, grains, or grain flour. Such food composition fortified with the compounds may be used in the preparation of foodstuffs, such as baked goods, meat products with fillers (e.g., hamburgers, sausages, etc.), cereals, pastas, and soups.

The cantharimide compositions or compounds may be included in food compositions which also contain a variety of other beneficial components. The optional components useful herein can be categorized by their healthful benefit or their postulated mode of action. However, it is to be understood that the optional components may in some instances provide more than one healthful benefit, or operate via more than one mode of action. Therefore, classifications of components herein are made for the sake of convenience, and are not intended to limit the component to the particular application or applications listed.

Cantharimide compositions may be in the form of dietary supplements or food additives, vitamins, precursors, and derivatives thereof. Minerals and/or amino acids can be added to the compositions. Vitamins may be in either natural or synthetic form. Suitable vitamin compounds include Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds. The vitamins may be included as the substantially pure material, or as an extract obtained by suitable physical and/or chemical isolation from natural (e.g., plant) sources.

In another embodiment, the cantharimide compounds and compositions may be added directly to foods, so that an effective amount of the compound is ingested during normal meals. Any methods known to those skilled in the art may be used to add to or incorporate the compositions or compounds into natural or processed foodstuff to make the food composition. Other optional components in a food additive include anti-caking agent, dessicant, food preservatives, food coloring, and artificial sweetner.

Dosage & Frequency of Administration

The amount of the cantharimide compound or composition which will be effective in the prevention, treatment, management, relief, or amelioration of an adverse health condition, a disorder, or one or more symptoms thereof may vary with the nature and severity of the disease or condition, and/or the route by which the active ingredient is administered. The frequency and dosage may also vary according to factors specific for each subject or patient, depending on the specific therapy administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of cantharimide include milligram or microgram amounts of cantharimide per kilogram of subject or sample weight (e.g., about 1 microgram per kilogram to about 50 milligrams per kilogram, about 10 micrograms per kilogram to about 5 milligrams per kilogram, or about 1 microgram per kilogram to about 20 micrograms per kilogram, or about 9 micrograms per kilogram).

The recommended daily dose range of a cantharimide compound may lie within the range of from about 0.01 mg to about 10 mg per day, given as a single once-a-day dose, or preferably as divided doses throughout one day. In one example, the daily dose is administered twice daily in equally divided doses. Specifically, a daily dose range may be from about 0.05 mg to about 5 mg per day, and more specifically between about 0.1 mg and about 2 mg per day. In managing the subject or patient, the therapy may be initiated at a lower dose, such as about 0.01 mg to about 0.25 mg, and may be increased if necessary up to about 2 mg to about 10 mg per day, as either a single dose or divided doses, depending on the subject or patient's global response. It may be necessary to use dosages of the active ingredient outside the ranges disclosed herein in some cases, as will be apparent to those of ordinary skill in the art. Furthermore, it is noted that the dietitian, clinician or treating physician will know how and when to interrupt, adjust, or terminate therapy in conjunction with individual patient response.

Different effective amounts may be applicable for different diseases and conditions, as will be readily known by those of ordinary skill in the art. Preferably, the amounts are sufficient to prevent, manage, treat or ameliorate such disorders, but insufficient to cause, (or are sufficient to reduce,) adverse effects associated with the cantharimide compounds. When a subject or patient is administered multiple dosages of a cantharimide compound, not all of the dosages need be the same. For example, the dosage administered to the subject or patient may be increased to improve the prophylactic or therapeutic effect of the compound, or it may be decreased to reduce one or more side effects that a particular subject or patient is experiencing.

In a specific example, the dosage of the cantharimide composition or a cantharimide compound administered to prevent, treat, manage, or ameliorate a disorder or one or more symptoms thereof in a patient is about 150 g/kg, preferably about 250 g/kg, about 500 g/kg, about 1 mg/kg, about 5 mg/kg, about 10 mg/kg, about 25 mg/kg, about 50 mg/kg, about 75 mg/kg, about 100 mg/kg, about 125 mg/kg, about 150 mg/kg, or about 200 mg/kg or more of a patient's body weight. In another example, the dosage of the cantharimide composition or a cantharimide compound administered to prevent, treat, manage, or ameliorate a disorder or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than cantharimide compounds, which have been used, or are currently being used, to prevent, treat, manage, or ameliorate a disorder or one or more symptoms thereof can be used in the combination therapies. Preferably, dosages lower than those which have been used, or are currently being used to prevent, treat, manage, or ameliorate a disorder, or one or more symptoms thereof are used in the combination therapies. The recommended dosages of agents currently used for the prevention, treatment, management, or amelioration of a disorder, or one or more symptoms thereof can obtained from any reference in the art.

One or more cantharimide compounds and one or more other the therapies may be cyclically administered. Cycling therapy involves the administration of a first therapy for a period of time, followed by the administration of a second therapy for a period of time, followed by the administration of a third therapy for a period of time and so forth, and repeating this sequential administration, in order to reduce the development of resistance to one of the agents, to avoid or reduce the side effects of one of the agents, and/or to improve the efficacy of the treatment.

For example, administration of the same cantharimide compound may be repeated, and the administrations may be separated by at least 1 day, 2 days, 3 days, 5 days, 10 days, 15 days, 30 days, 45 days, 2 months, 75 days, 3 months, or 6 months. In another example, administration of the same prophylactic or therapeutic agent may be repeated, and the administration may be separated by at least at least 1 day, 2 days, 3 days, 5 days, 10 days, 15 days, 30 days, 45 days, 2 months, 75 days, 3 months, or 6 months.

A method of preventing, treating, managing, or ameliorating a disorder, or one or more symptoms thereof, includes administering to a subject in need thereof a dose of at least 150 g/kg, preferably at least 250 g/kg, at least 500 g/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the cantharimide once every 3 days. Preferably the compound(s) are administered once every 4 days, once every 5 days, once every 6 days, once every 7 days, once every 8 days, once every 10 days, once every two weeks, once every three weeks, or once a month.

Biological Assays

The cantharimide compositions and compounds may be assayed for their ability to modulate cell proliferation, cell growth and cell cycle progression. Techniques known to those in art, include, but are not limited to, $^3$H-thymidine incorporation, trypan blue cell counts, and fluorescence activated cell sorting ("FACS") analysis. The cantharimide compositions can also be assayed for their ability to induce cytolysis. Cytolysis can be assessed by techniques known to those in art, including, but not limited to, $^{51}$Cr-release assays. The cantharimide compositions can also be assayed for their ability to inhibit cell migration, cell adhesion angiogenesis or tubulin polymerization using techniques well-known to one of skill in the art or described herein. The cantharimide compositions and compound can also be assayed for their ability to induce cell cycle arrest or apoptosis.

The cantharimide compositions can be tested in suitable animal model systems prior to use in humans. Such animal model systems include rats, mice, chicken, cows, monkeys, pigs, dogs, rabbits, etc. Any animal system well-known in the art may be used. In a specific embodiment, the cantharimide compositions and compounds are tested in a mouse model system. Such model systems are widely used and well-known to the skilled artisan. Pharmaceutical compositions or compounds can be administered repeatedly. Several aspects of the procedure may vary including temporal regime for administration of the cantharimide compositions or compounds.

The toxicity and/or efficacy of the cantharimide compositions may be determined by standard pharmaceutical procedures in cell cultures or experimental animals. Examples include determining the $GI_{50}$ (the growth inhibition of 50% of the population), the $LD_{50}$ (the dose lethal to 50% of the population) and the $ED_{50}$ (the dose therapeutically effective in 50% of the population). The dose ratio between toxic and therapeutic effects is the therapeutic index which can be expressed as the ratio $LD_{50}/GI_{50}$ or $LD_{50}/ED_{50}$. Compositions and compounds of the cantharimides that exhibit large therapeutic indices are preferred. While compositions and compounds that exhibit toxic side effects may be used, care should be taken to design a delivery system that targets such compositions and compounds to the site of affected tissue in order to minimize potential damage to uninfected cells and, thereby, reduce side effects.

The data obtained from the cell culture assays and animal studies can be used in formulating a range of dosage of the compositions and compounds for use in humans. The dosage of such agents lies preferably within a range of circulating concentrations that include the $ED_{50}$ with little or no toxicity. The dosage may vary within this range, depending upon the dosage form employed and the route of administration utilized. For any agent used in the method, the therapeutically effective dose can be estimated initially from cell culture assays. A dose may be formulated in animal models to achieve a circulating plasma concentration range that includes the IC$_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography (HPLC) and radioimmunasssay (RIA). The pharmacokinetics of a prophylactic or therapeutic can be determined, e.g., by measuring parameters such as peak plasma level ($C_{max}$), area under the curve (AUC, which is measured by plotting plasma concentration of the agent versus time, and reflects bioavailability), half-life of the compound ($t_{1/2}$), and time at maximum concentration.

Efficacy in preventing or treating a proliferative disorder such as cancer may be demonstrated, such as by detecting the ability of the cantharimide compositions to reduce one or more symptoms of the proliferative disorder, to reduce the proliferation of cancerous cells, to reduce the spread of cancerous cells, or to reduce the size of a tumor.

METHOD OF PREPARATION

Preparation of Cantharimide of Formula (1)

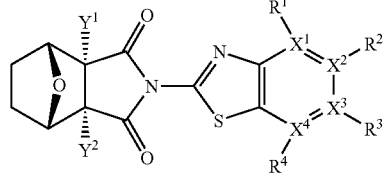

formula (1)

Cantharimides may be derived from cantharidin and 2-amino-benzothiazole derivatives, using the standard "one-pot" condensation reaction, as shown in Scheme 1. The 2-aminobenzothiazole derivatives may be either commercially available or prepared following a standard protocol from aniline. Under Scheme 1, condensation of the 2-aminobenzothiazole with cantharidin in the presence of toluene:triethylamine mixture (3:1) may give the corresponding imide in moderate to high yield. Consequently, Scheme 1 may enable multiple and parallel synthesis of cantharimide libraries.

Scheme 1

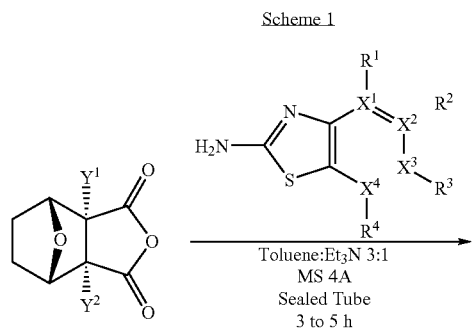

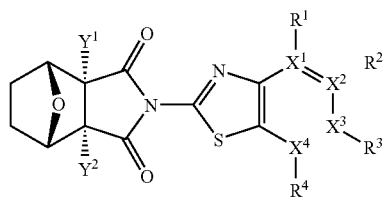

Preparation of 2-Amino-6-carboxybenzothiazole of Formula (2)

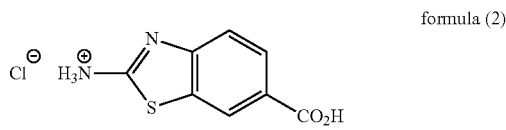 [SMILES: [Cl-] ; [NH3+]c1nc2ccc(C(=O)O)cc2s1]

formula (2)

A solution of 4-aminobenzoic acid (1.37 g, 14 mmol) in AcOH (16 mL) may be added with potassium thiocyanate (3.9 g, 40 mmol) and may be stirred for 15 minutes. A solution of bromine (0.5 mL, 10 mmol) in AcOH (6 mL) may then be added slowly into the reaction mixture in water bath, where the temperature may be maintained at about 25° C. The resulting mixture may be stirred overnight. The mixture may then be filtered, and the pale yellow precipitate may then be further recrystallized with the minimal volume of aqueous hydrochloric acid (6 M). A pale yellow product of formula (2) may be collected with the following characterization: $^1$H NMR (CD$_3$OD, 500 MHz): δ 4.96 (2H, brs), 7.58 (1H, d, J=8.0 Hz), 8.14 (1H, dd, J=8.5 Hz and 1.5 Hz), 8.47-8.47 (1H, m); $^{13}$C NMR (CDCl$_3$): δ 12.1, 23.7, 54.6, 85.0, 85.1, 122.5, 123.9, 127.9, 128.3, 132.7, 151.9, 155.3, 168.0, 178.7.

Preparation of Cantharimide of Formula (3)

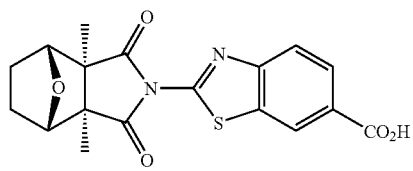

formula (3)

A mixture of cantharidin (50 mg, 0.26 mmol), 2-amino-6-carboxybenzothiazole (294 mg, 1.27 mmol), and a mixture of dried toluene and dried triethylamine (4 mL; 2:1, v/v) may be sealed in a tube and heated for 3 hours at 180° C. The reaction mixture may be concentrated, followed by flash chromatography (dichloromethane:methanol, 10:1) that may give the product CAN039 (51.9 mg, 55%) of formula (3) as a white solid with the following characterization: mp=180-181° C.; R$_f$=0.27 (hexane:acetone, 2:1); $^1$H NMR (CD$_3$OD, 500 MHz): δ 1.34 (6H, s), 1.72-1.74 (2H, m), 1.97-2.00 (2H, m), 4.69-4.70 (2H, m), 8.08 (1H, d, J=8.5 Hz), 8.18 (1H, dd, J=8.5 Hz and 1.5 Hz), 8.70-8.71 (1H, m); $^{13}$C NMR (CDCl$_3$): δ 12.1, 23.7, 54.6, 85.0, 85.1, 122.5, 123.9, 127.9, 128.3, 132.7, 151.9, 155.3, 168.0, 178.7; MS (EI) m/z (%): 372 (M+); HRMS calcd. for $C_{18}H_{16}N_2O_5S$ [M]+ found 358.0776.

Preparation of Cantharimide of Formula (4)

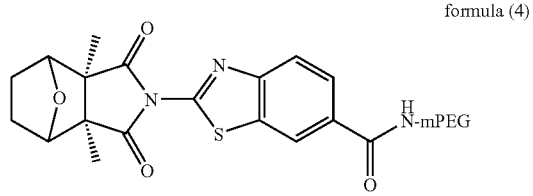

formula (4)

A mixture of CAN039 (50 mg, 0.13 mmol), N-(3-Dimethylaminopropyl)-N'-ethylcarbodiimide hydrochloride (31 mg, 0.16 mmol), dimethylaminopyridine (21.0 mg, 0.17 mmol) and mPEG(5000)-NH$_2$ (1 g, 0.2 mmol) in DCM (15 mL) may be stirred for 48 hours under N$_2$ atmosphere. The reaction mixture may be concentrated, followed by flash chromatography (dichloromethane:methanol, 10:1 to 6:1) that may give the product PEG-CAN039 MP (560 mg, 78%) of formula (4) as a white solid with the following characterization: mp=180-181° C.; $R_f$=0.27 (dichloromethane:methanol, 10:1); $^1$H NMR (CDCl$_3$, 500 MHz): δ 1.31 (6H, s), 1.77-1.83 (2H, m), 1.86-1.91 (2H, m), 3.37 (3H, s), 3.49-3.78 (576H, m), 4.76-4.77 (2H, m), 7.95 (1H, dd, J=8.5 Hz and 1.5 Hz), 8.12 (1H, d, J=8.5 Hz), 8.48-8.48 (1H, m); $^{13}$C NMR (CDCl$_3$): δ 12.1, 23.7, 54.6, 85.0, 85.1, 122.5, 123.9, 127.9, 128.3, 132.7, 151.9, 155.3, 168.0, 178.7.

Cell Lines and Cell Culture

An acute myelogenous leukaemia (AML) cell line (KG1a) and a hepatocellular carcinoma (HCC) cell line (Hep3B) may be obtained from American Type of Culture Collection (ATCC). The AML cell line may be maintained in RPMI 1640 (JRH Biosciences) supplemented with 10% of heat inactivated fetal bovine serum (Hyclone), together with antibiotics including penicillin and streptomycin. The Hep3B HCC cell line may be maintained in DMEM with 10% of heat inactivated fetal bovine serum (Hyclone), together with antibiotics including penicillin and streptomycin. Cells may be allowed to grow in a humidified cell culture incubator kept at 5% carbon dioxide.

Human Bone Marrow Cells Collection and Isolation

Non-malignant hematological disorder bone marrow cells may be collected by a bone marrow aspirate method from consented patients from clinical wards of Prince of Wales Hospital (Hong Kong, China), according to the regulation of the Hospital. Immediately after collection, mononuclear cells may be enriched by Ficoll Plaque (available from General Electricity) gradient centrifugation. Cells may be washed twice by phosphate buffered saline and resuspended in complete medium. Viable cell percentage may then be estimated by trypan blue exclusion assay and counted using a haemacytometer.

EXPERIMENTAL DATA

The characterization of different cantharimide structures from reaction scheme 1 is shown in Table 2 below. The cantharimide compounds may be soluble in methoxyl polyethylene glycol (mPEG(5k)). For example, the solubility of Can039 is 5 mg/20 l of DMSO, and the solubility of Can039-PEG is 10 mg/1 DDI water.

TABLE 2

Characterization of different cantharimide structures

| Entry | Structure | 6-Subsituting group | Log P* | $\pi_{sub}$ | IC$_{50}$ Hep3B (g/ml) | Solubility in water |
|---|---|---|---|---|---|---|
| 1 | 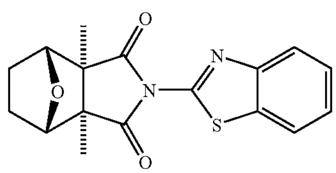 [SMILES: C[C@@]12C(=O)N(c3nc4ccccc4s3)C(=O)[C@]1(C)[C@H]1CC[C@@H]2O1] | H | 3.39 | — | ~6 | Poor |
| 2 | 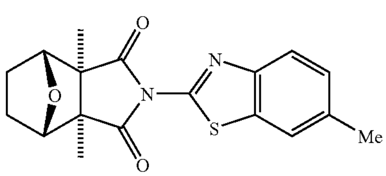 [SMILES: Cc1ccc2nc(N3C(=O)[C@@]4(C)[C@@H]5CC[C@@H](O5)[C@@]4(C)C3=O)sc2c1] | Me | 3.88 | 0.49 | ~20 | Poor |
| 3 | 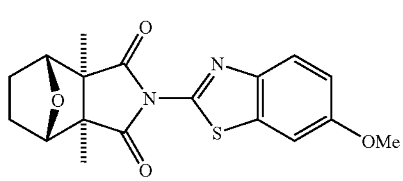 [SMILES: COc1ccc2nc(N3C(=O)[C@@]4(C)[C@@H]5CC[C@@H](O5)[C@@]4(C)C3=O)sc2c1] | OMe | 3.27 | −0.12 | ~5 | Poor |

TABLE 2-continued
Characterization of different cantharimide structures
| Entry | Structure | 6-Subsituting group | Log P* | $\pi_{sub}$ | IC$_{50}$ Hep3B (g/ml) | Solubility in water |
|---|---|---|---|---|---|---|
| 4 | 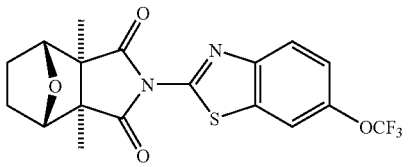 [SMILES: C[C@@]12C(=O)N(c3nc4ccc(OC(F)(F)F)cc4s3)C(=O)[C@]1(C)[C@H]1CC[C@@H]2O1] | OCF$_3$ | 4.92 | 1.53 | ~10 | Fair |
| 5 | 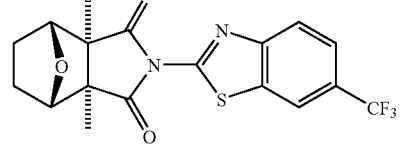 | CF$_3$ | 4.32 | 0.93 | ~5 | Fair |
| 6 | 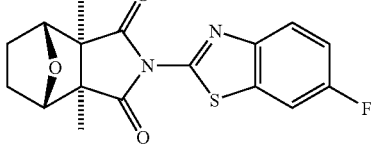 | F | 3.55 | 0.16 | ~5 | Poor |
| 7 | 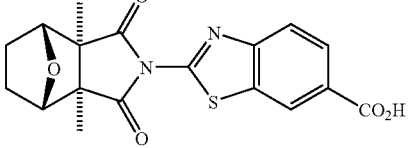 | CO$_2$H | 2.95 | −0.44 | ~5 | Good |
| 8 | 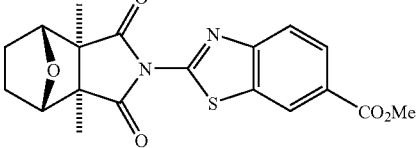 | CO$_2$Me | 3.21 | −0.18 | ^N.D | Good |
| 9 | 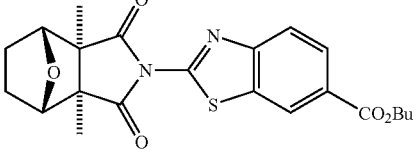 | CO$_2$Bu | 4.46 | 1.07 | ^N.D | Good |
| 10 | 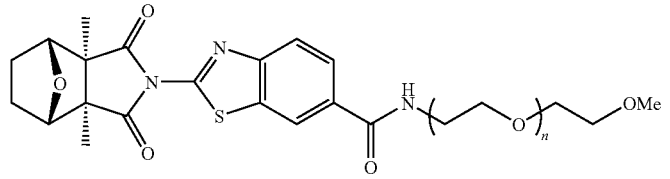 | CONHmPEG(5k) | — | | ~250 | Excellent |
| 11 | 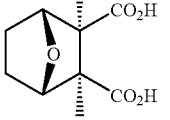 | — | 0.7 | — | ~0.25 | Excellent |
*LogP values as predicted using ChemDraw Ultra 9
^N.D: Not determined The following examples are provided to illustrate one or more preferred embodiments of the cantharimide. Numerous variations may be made to the following examples that lie within the scope of the invention.

EXAMPLES

Example 1

MTS ([3-(4,5-dimethylthiazol-2-yl)-5-(3-carboxymethoxyphenyl)-2-(4-sulfophen-yl)-2H-tetrazolium]) Assay The effect of the synthesized cantharimides on the growth of the cell lines described above was investigated in vitro using a standard MTS ([3-(4,5-dimethylthiazol-2-yl)-5-(3-carboxymethoxyphen-yl)-2-(4-sulfophenyl)-2H-tetrazolium]) assay. Changes in the cellular viability of cell that include Hep3B and SKHep-1 with cantharidin analogues were monitored using the MTS activity assay. In particular, $1 \times 10^4$ hepatoma carcinoma cells (SK-Hep-1) were seeded at day 0. For the MTS assay, the medium was changed after 24 hours, and various compounds were added at different concentrations. For bone marrow cells, compounds were added at the same day as the seeding. After 48 hours of incubation, the medium was removed, and MTS/PMS solution was added. The added medium was incubated for exactly 30 minutes. Subsequently, optical absorbance was determined at 490 nm using an optical absorbance detector (available from Promega).

More than 30 cantharimides were screened for their effects on cell proliferation and potential cytotoxicity in the two cell lines of Hep3B and SKHep-1. The activities of cantharimide were monitored in the presence of dicantharidic (a commercially available cantharidin-mimic) as a reference control. The results in Table 1 show that most cantharimides showed considerable suppressing effects on cancer cell growth with $IC_{50}$ values ranging from 5 to 20 g/ml.

Example 2

In Vitro Studies of Cantharimide—MTS Assays

The cytotoxic activity of cantharimide of formula (3) using a leukemia cell line KG1a was investigated by means of a MTS assay. The $MTS_{50}$ activity was measured as the concentration necessary for 50% of MTS reduction ability by the chemical treated cell as compared with the control. The dicantharidic acid in in vitro studies showed a value of about 0.5 g/ml for $MTS_{50}$ activity. On the other hand, cantharimide gave a value of about 5 g/ml for $MTS_{50}$ activity against the same cancer cell line.

These results showed that the dicantharidic acid exhibited a 10-fold activity to the cancer cell line when compared to cantharimide. However, dicantharidic acid was shown to remain extremely toxic at a concentration of down to 0.15625 g/ml after 48 hours of incubation for primary culture of non-malignant haematological disorder bone marrow cells. Consequently, while cantharimide demonstrated a relatively weaker inhibition of tumor cell proliferation, its lack of cytotoxic activity would help to increase the survival rate of patient.

Example 3

In Vitro Studies of Cantharimide—Morphology Assay

The toxicity on non-malignant haematological bone marrow sample was tested to evaluate the side effects of cantharidin, which included bone marrow suppression, and gastrointestinal and urinary tract toxicity.

The morphological effect of cytotoxic action of cantharidic acid and cantharimide on leukemia cells are depicted in FIGS. 1A to 1F. The untreated non-malignant haematological disorder bone marrow and KG1a AML cell lines are depicted in FIGS. 1A and 1D, respectively. The non-malignant haematological disorder bone marrow and KG1a AML cell lines treated with 5 g/mL of dicantharidic acid are depicted in FIGS. 1B and 1E, respectively. The non-malignant haematological disorder bone marrow and KG1a AML cell lines treated with 5 g/mL of cantharimide are depicted in FIGS. 1C and 1F, respectively.

The results show that both dicantharidic acid and cantharimide induced loss of colony formation potential and cell shrinkage to the leukemia cells at a dose of 5 g/ml after 48 hours incubation, as depicted in FIGS. 1E and 1F, respectively. The results further show that dicantharidic acid induced a similar loss to the bone marrow cells, as depicted in FIG. 1B. On the other hand, the colony formation remained unchanged using cantharimide, as depicted in FIG. 1C.

These results demonstrate that, while the potency of cantharimide towards cancer cells was comparable to that of cantharidin, cantharimide had a remarkable decrease of cytotoxic response on the normal bone marrow cell line. Since a lower toxic effect is exhibited, cantharimide may provide an improved therapeutic advantage over the traditional cantharidin. This may overcome the high toxicity of most chemotherapeutic agents that remains a major obstacle to cancer drug development, as well as to chemotherapy in cancer treatment.

Example 4

In Vivo Xenograft Animal Model for the Studies of Cantharimide

Athymic nude mice purchased from the Chinese University of Hong Kong (Hong Kong, China) with average body weight of 25 g were injected subcutaneously with the human hepatocellular carcinoma (HCC) cell line Hep3B. The mice were housed in a sterile condition, where their tumor size was measured daily using an electronic caliper. When tumor size reached a mean tumor volume of about 150 mm$^3$, calculated by the formula (length*width*width)/2, the mice were randomly divided into two groups of three mice. One of the groups was treated with pegylated cantharimide (CAN039 MP) of formula (4) at a concentration of 20 mg/Kg body weight/day by intraperitoneal injection for seven consecutive days starting from day zero. The other group received only carrier (mPEG(5k))-NH$_2$ as a control.

Figure 2:
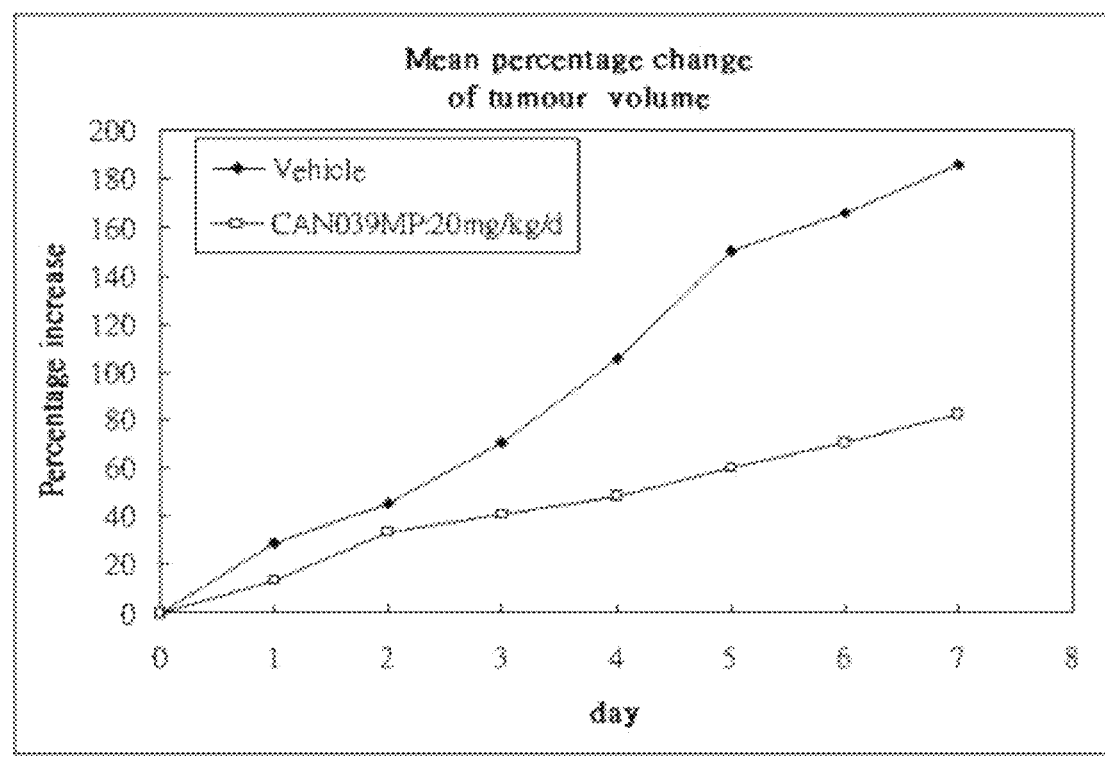
FIG. 2 depicts a graph of a mean percentage change of tumor volume of a carrier control and pegylated cantharimide to a Hep3B HCC xenograph tumor growth in mice.

The results were expressed as the relative mean changes of tumor volume compared with the original size of the tumor at day zero. As shown in FIG. 2, pegylated CAN039 MP delayed the Hep3B HCC xenograft tumor growth by a mean volume of about 50% when compared with the carrier control.

Figure 3:
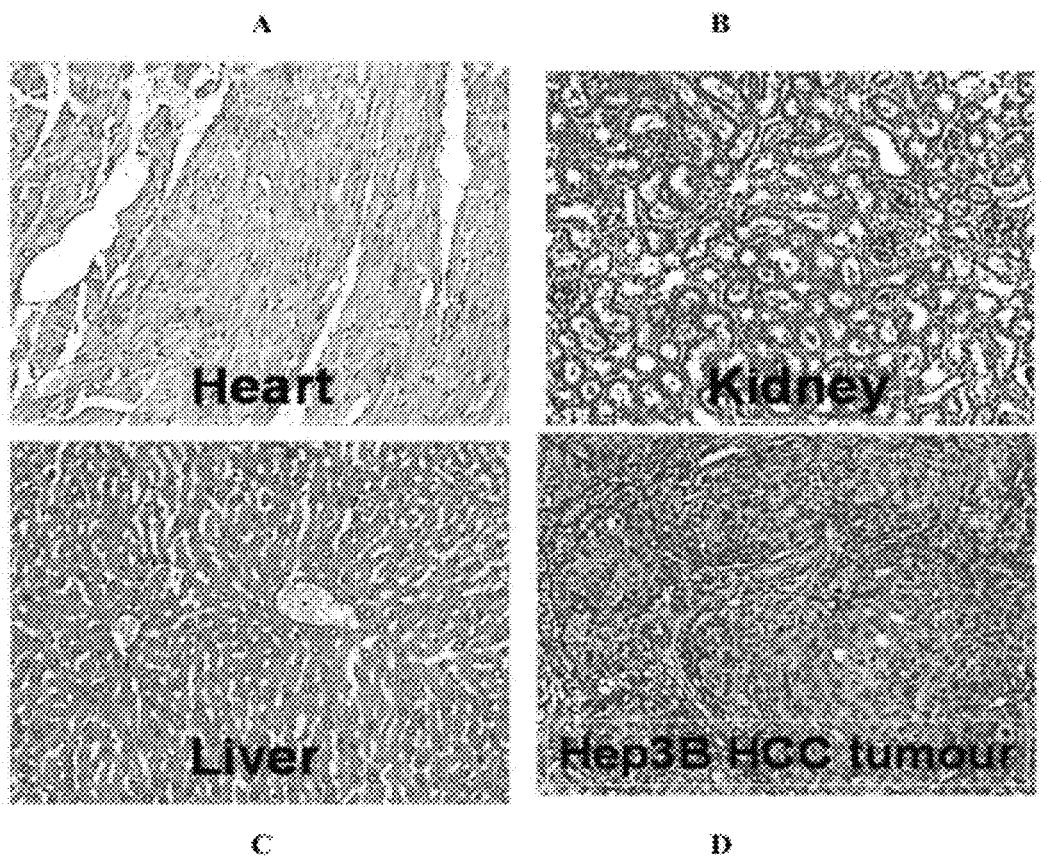
FIG. 3A depicts an image of a heart autopsy analysis from a pegylated CAN039 MP administrated animal.
FIG. 3B depicts an image of a kidney autopsy analysis from a pegylated CAN039 MP administrated animal.
FIG. 3C depicts an image of a liver autopsy analysis from a pegylated CAN039 MP administrated animal.
FIG. 3D depicts an image of a Hep3B HCC tumor.

FIGS. 3A to 3C depicts images of a heart, kidney and livery autopsy analysis, respectively, from a pegylated CAN039 MP-treated animal. An image of a Hep3B HCC tumor is depicted in FIG. 3D, showing necrotic tissues. As shown, the autopsy analysis from the pegylated CAN039 MP-administrated animals did not show significant toxicology effects from the vital organs, as no necrotic tissues were observed.

Consequently, the results show that pegylation of cantharimides shows effectively retarded tumor growth from athymic nude mice with human hepatocellular carcinoma xenograft without significant toxicity.

CONCLUSION

The facile one-step coupling of cantharidin with 2-aminobenzothiazole derivatives may be used to synthesize a large number of small molecule inhibitors, and may open a new regimen for the treatment for cancers of varying etiologies. The PEG-CAN039 cantharimide provided a water-soluble version of cantharimide that may find benefits in prolongation of serum level of drug, decreased renal clearance, and protection of antibody formation. Cantharimides have been synthesized to show anti-tumor effect as a cantharidin-mimic, and showed a dose-dependant inhibition of tumor cell proliferation over the range from 5 to 6 g/ml, as disclosed in Examples 4. In terms of MTS activity, the studies in Examples 2 demonstrated that the introduction of a carboxylic group at the 6-position of 2-aminobenzothiazole enhanced the cytotoxicity of the compound to cancer cells, while reducing the toxicity to normal cells, providing a potential benefit to chemotherapy. Since a lower toxic effect is exhibited in Example 3, cantharimide provided an improved therapeutic advantage over the traditional cantharidin. The results further showed effective retardation of tumor growth from athymic nude mice with human hepatocellular carcinoma xenograft without significant toxicity, as seen in Example 5.

While the examples of the cantharimide composition have been described, it should be understood that the cantharimide composition not so limited and modifications may be made. The scope of the cantharimide composition is defined by the appended claims, and all devices that come within the meaning of the claims, either literally or by equivalence, are intended to be embraced therein.

What is claimed is:

1. A cantharimide compound, comprising the background of formula (1):

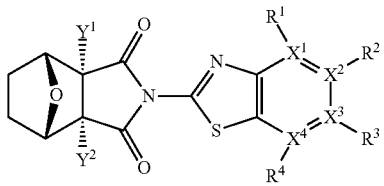

wherein, $R^1$, $R^2$, $R^3$, and $R^4$ are independently selected from the group consisting of H, $C(O)OR^5$, $C(O)R^6$, $C(O)NR^7R^8$, $NR^9C(O)R^{10}$, $N-R^{11}R^{12}$, $O-R^{13}$, $S-R^{14}$, $P(O)(OR^{15})(OR^{16})$, $As(O)(OR^{17})(OR^{18})$, $SO_2R^{19}$, $SO_3R^{20}$, and $B(OR^{21})$, wherein the $R^1$ to $R^4$ are not all hydrogen with the proviso that $R^3$ is not hydrogen;

wherein the $X^1$ to $X^4$ are carbon; and wherein the $Y^1$, $Y^2$ and $R^5$ to $R^{21}$ are independently selected from the group consisting of hydrogen, $C_{1-12}$-alkyl, aryl, heteroaryl, and a bioactive polymer comprising:

(i) a polymer moiety from 2 to 300 monomer units; and (ii) a terminal moiety connected to the polymer moiety at the ω-position, provided that the cantharimide compound is neither

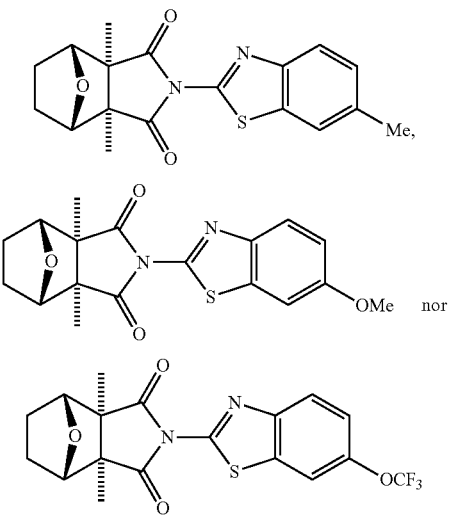

and a pharmaceutically acceptable salt, solvate or hydrate thereof.

2. The cantharimide compound of claim 1, wherein the cantharimide compound is selected from the group consisting of

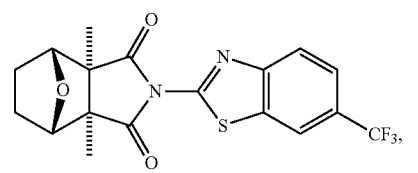

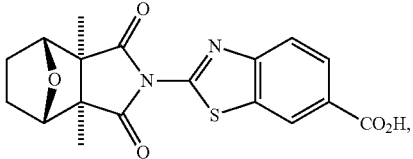

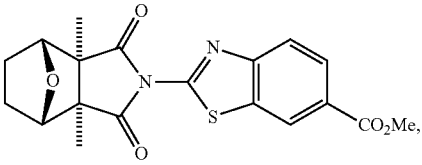

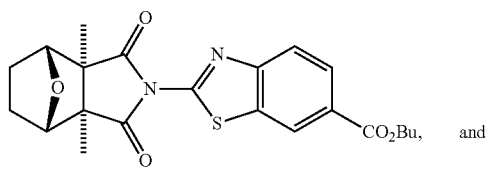

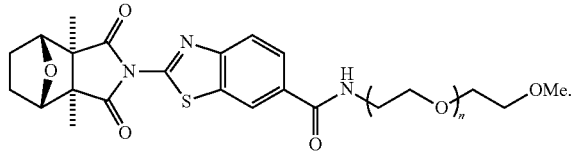

3. The cantharimide compound of claim 2, wherein the cantharimide compound is

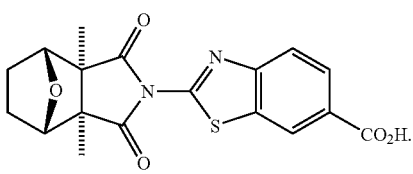 [SMILES: C[C@@]12C(=O)N(c3nc4ccc(C(=O)O)cc4s3)C(=O)[C@]1(C)[C@H]1CC[C@@H]2O1]

4. The cantharimide compound of claim 2, wherein the cantharimide compound is

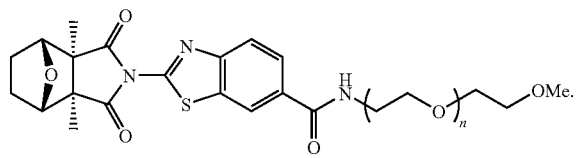

5. The cantharimide compound of claim 1, wherein the polymer moiety is selected from the group consisting of poly(alkylene oxides), poly(oxyethylated polyols), and poly(olefinic alcohols).

6. The cantharimide compound of claim 1, wherein the terminal moiety is selected from the group consisting of a propionate moiety and a butanoate moiety.

7. The cantharimide compound according to claim 1, wherein the cantharimide compound is pegylated.

8. The cantharimide compound according to claim 7, wherein the cantharimide compound is

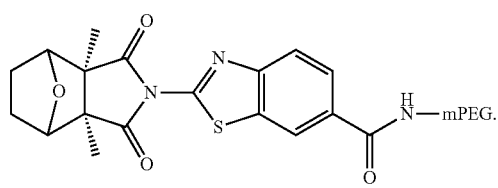

9. A pharmaceutical composition comprising
(i) a cantharimide compound comprising the background of formula (1):

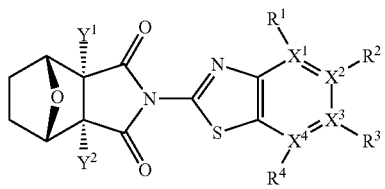

wherein, $R^1$, $R^2$, $R^3$, and $R^4$ are independently selected from the group consisting of H, $C(O)OR^5$, $C(O)R^6$, $C(O)NR^7R^8$, $NR^9C(O)R^{10}$, $N-R^{11}R^{12}$, $O-R^{13}$, $S-R^{14}$, $P(O)(OR^{15})(OR^{16})$, $As(O)(OR^{17})(OR^{18})$, $SO_2R^{19}$, $SO_3R^{20}$, and $B(OR^{21})$,
wherein the $R^1$ to $R^4$ are not all hydrogen with the proviso that $R^3$ is not hydrogen;
wherein the $X^1$ to $X^4$ are carbon; and
wherein the $Y^1$, $Y^2$ and $R^5$ to $R^{21}$ are independently selected from the group consisting of hydrogen, $C_{1-12}$-alkyl, aryl, heteroaryl, and a bioactive polymer comprising:
(i) a polymer moiety from 2 to 300 monomer units; and
(ii) a terminal moiety connected to the polymer moiety at the ω-position, provided that the cantharimide compound is neither

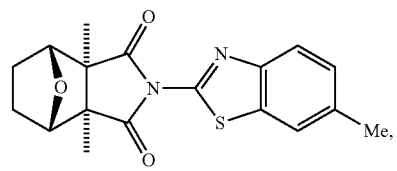

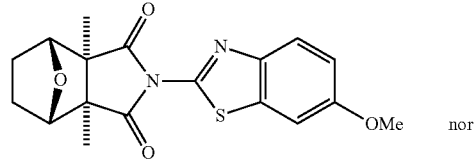

nor

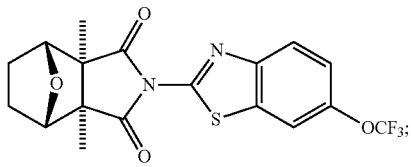

and
a pharmaceutically acceptable salt, solvate or hydrate thereof; and
(ii) a pharmaceutical acceptable carrier.

10. The pharmaceutical composition according to claim 9, wherein the cantharimide compound is selected from the group consisting of

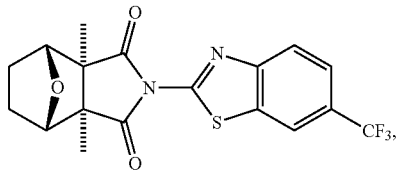

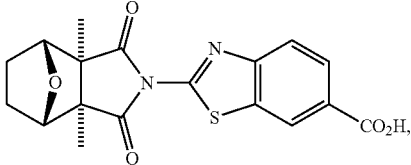

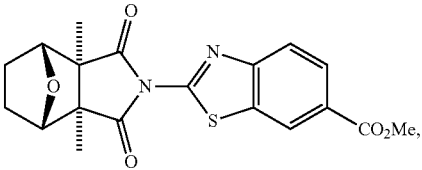

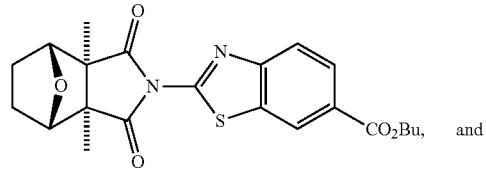

and

-continued

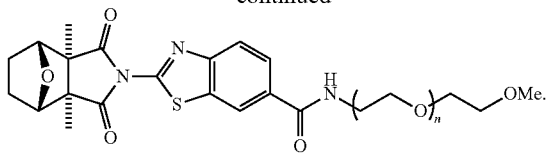

11. The pharmaceutical composition according to claim 9, wherein the cantharimide compound is

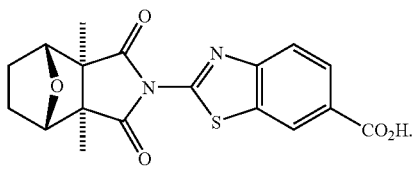 [SMILES: C[C@@]12C(=O)N(c3nc4ccc(C(=O)O)cc4s3)C(=O)[C@]1(C)[C@H]1CC[C@@H]2O1]

12. The pharmaceutical composition according to claim 9, wherein the cantharimide compound is

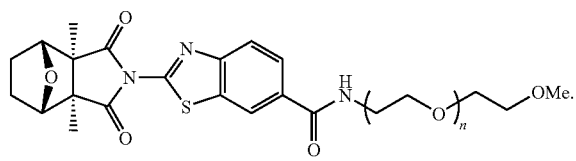

13. The pharmaceutical composition according to claim 9, wherein the polymer moiety is selected from the group consisting of poly(alkylene oxides), poly(oxyethylated polyols), and poly(olefinic alcohols).

14. The pharmaceutical composition according to claim 9, wherein the terminal moiety is selected from the group consisting of a propionate moiety and a butanoiate moiety.

15. The pharmaceutical composition according to claim 9, wherein the cantharimide compound is pegylated.

16. The pharmaceutical composition according to claim 15, wherein the cantharimide compound is

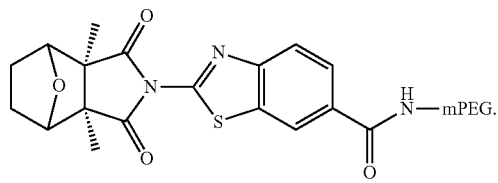

17. The pharmaceutical composition according to claim 9, further comprising
(iii) an anti-cancer agent.

18. The pharmaceutical composition according to claim 17, wherein the anti-cancer agent is selected from the group consisting of acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates, pamidronate (Aredria®), sodium clondronate (Bonefos®), zoledronic acid (Zometa®), alendronate (Fosamax®), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin-2, interferon alpha 2a; interferon alpha 2b; interferon alpha n1; interferon alpha n3; interferon beta I a; interferon gamma I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

19. The pharmaceutical composition according to claim 17, wherein the anti-cancer agent is selected from the group consisting of 20 epi 1,25 dihydroxyvitamin D3; 5 ethynyluracil; abiraterone; aclarubicin; acylfulvene; adecypenol; adozelesin; aldesleukin; tyrosine kinase antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; Avastin®; azasetron; azatoxin; azatyrosine; baccatin III derivatives; balanol; batimastat; BCR/ABL antagonists; benzochlorins; benzoylstaurosporine; beta lactam derivatives; beta alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL 2; capecitabine; carboxamide amino triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors; atorvastatin, cerivastatin, fluvastatin, lescol, lupitor, lovastatin, rosuvastatin, and simvastatin; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubicin; ipomeanol, 4; iroplact; irsogladine; isobengazole; isohomohalicondrin B; itasetron; jasplakinolide; kahalalide F; lamellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anticancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum triamine complex; porfimer sodium; porfiromycin; prednisone; propyl bis acridone; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

\* \* \* \* \*